United States Patent [19]

Gebert et al.

[11] 4,358,450
[45] Nov. 9, 1982

[54] O-ALKYLATED OXIMES AND PHARMACEUTICAL COMPOSITION THEREOF

[75] Inventors: Ulrich Gebert; Ernold Granzer, both of Kelkheim; Heinz-Günter Greve, Frankfurt am Main; Werner Thorwart, Wiesbaden, all of Fed. Rep. of Germany

[73] Assignee: Hoechst Aktiengesellschaft, Frankfurt am Main, Fed. Rep. of Germany

[21] Appl. No.: 63,810

[22] Filed: Aug. 6, 1979

Related U.S. Application Data

[63] Continuation of Ser. No. 864,004, Dec. 23, 1977, abandoned.

[30] Foreign Application Priority Data

Dec. 24, 1976 [DE] Fed. Rep. of Germany ....... 2658762

[51] Int. Cl.³ ................. A61K 31/495; C07D 241/06
[52] U.S. Cl. .................................. 424/250; 424/263; 424/258; 424/267; 544/360; 544/362; 544/363; 544/372; 544/373; 544/376; 544/379; 544/394; 546/176; 546/191; 546/194; 546/200; 546/201; 546/202; 546/205; 546/208; 546/214; 546/232; 542/416
[58] Field of Search ............. 544/360, 362, 363, 372, 544/373, 376, 379, 394; 546/176, 191, 194, 200, 201, 202, 205, 208, 214, 232; 542/416; 424/250, 263, 258, 267

[56] References Cited

U.S. PATENT DOCUMENTS

| | | |
|---|---|---|
| 3,060,177 | 10/1962 | Druey et al. ..................... 542/416 |
| 3,590,037 | 6/1971 | Benko et al. ..................... 542/416 |
| 3,692,835 | 9/1972 | Van Dijk et al. ................. 542/416 |
| 3,947,446 | 3/1976 | Witte et al. ....................... 424/250 |
| 4,000,274 | 12/1977 | Renth et al. ....................... 424/250 |
| 4,038,317 | 7/1977 | Wermuth et al. ............. 260/566 EA |
| 4,083,978 | 4/1978 | Budal et al. ....................... 424/250 |

FOREIGN PATENT DOCUMENTS 842968  8/1960  United Kingdom ............... 542/416

Primary Examiner—Arthur P. Demers
Attorney, Agent, or Firm—Quaintance & Murphy

[57] ABSTRACT

Compounds of general formula

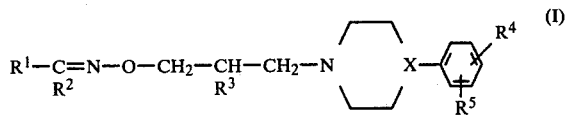

wherein $R^1$ represents a member selected from the group consisting of
(a) an unsubstituted at most binuclear aryl group having from 6 to 10 carbon atoms, such groups substituted by from 1 to 3 equal or different radicals selected from the group consisting of alkyl, halogenoalkyl, alkoxy, dialkylamino each having up to 4 carbon atoms in the alkyl moiety, halogen phenyl, carboxyl, cyano, nitro and hydroxy groups,
(b) a 5- to 6-membered heteroaromatic ring wherein the heteroatom is selected from nitrogen, oxygen and sulfur atoms and such rings anellated to a benzene nucleus;
$R^2$ represents a member selected from the group consisting of hydrogen, alkyl having up to 3 carbon atoms, phenyl, cycloalkyl having up to 6 carbon atoms in the ring and cycloalkyl bearing a hydrocarbon bridging radical having up to 2 carbon atoms;
$R^3$ represents hydrogen, hydroxy or acyloxy;
$R^4$ and $R^5$ are the same or different and each represents a member selected from the group consisting of halogen, alkyl, and halogenoalkyl each having up to 3 carbon atoms, and nitro; and
X represents nitrogen or methine
and physiologically acceptable acid addition salts thereof and a pharmaceutical composition containing said compounds.

10 Claims, 3 3 Drawing Figures

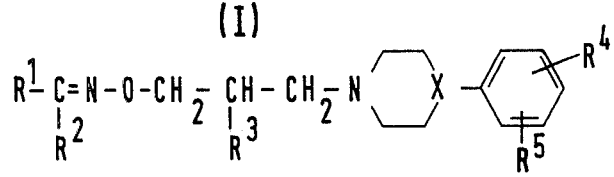 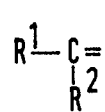
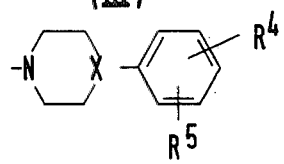 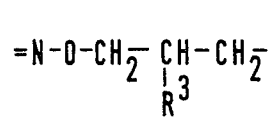 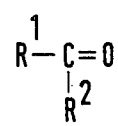
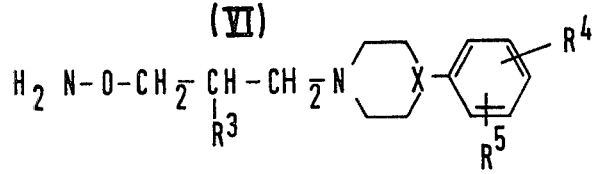
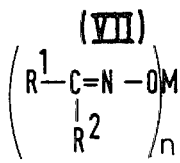 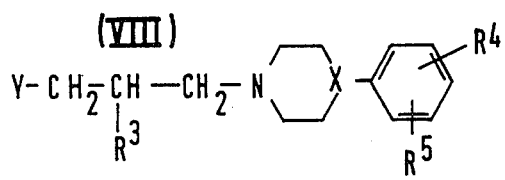
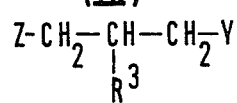
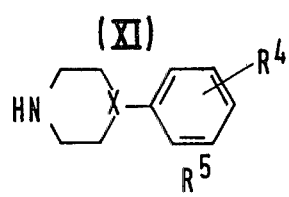 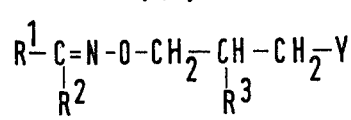

(XII) 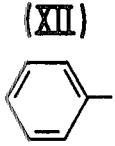 (XIII) 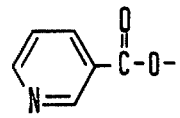 (XIV) 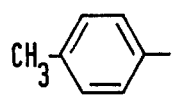 (XV) 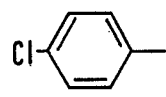
(XVI) 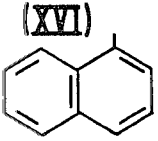 (XVII) 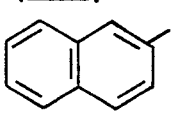 (XVIII) 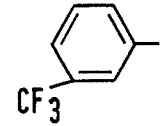 (XIX) 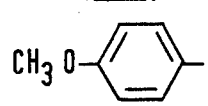
(XX) 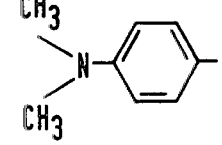 (XXI) 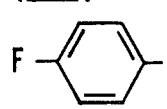 XXII 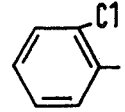 XXIII 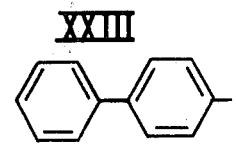
(XXIV) 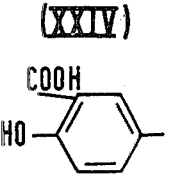 (XXV) 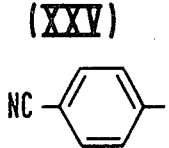 (XXVI) 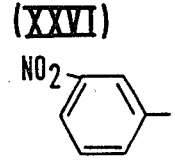 (XXVII) 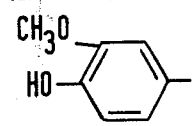
(XXVIII) 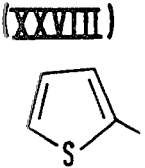 (XXIX) 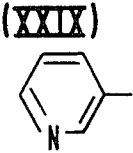 (XXX) 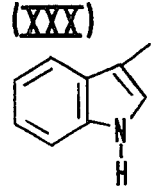 (XXXI) 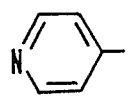
XXXIII 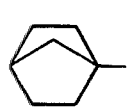 (XXXII) 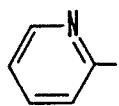

O-ALKYLATED OXIMES AND PHARMACEUTICAL COMPOSITION THEREOF

This is a continuation of copending application Ser. No. 864,004, filed Dec. 23, 1977, now abandoned.

This invention relates to novel O-alkylated oximes having interesting pharmacological properties.

Research has hitherto been directed towards obtaining pharmacologically active compounds having therapeutic benefits by reacting salicylic acid aldehydes with O-[2-(4-morpholinyl)-ethyl]-hydroxylamine, oximes with diethylamino-, morpholino-, pyrrolidino- and 4-methylpiperazinoalkyl halides and by reacting O-(2,3-epoxypropyl)-oximes with ammonia, dimethyl-, diethyl-, n-propyl-, isopropyl- and tert.-butyl-amine.

We have now surprisingly found that pharmacologically highly active compounds may be obtained by introducing a 4-phenyl-piperazinyl or 4-phenylpiperidinyl group into the side chain of O-propylated oximes. We have found that the principal activity of these derivatives is the capacity to decrease blood cholesterol and triglyceride levels.

Thus, according to one aspect of the present invention there are provided compounds of general formula

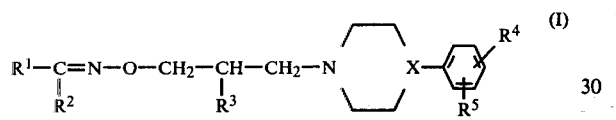
(I)

(wherein $R^1$ represents (a) a mono- or binuclear aryl group having from 6 to 10 carbon atoms, optionally substituted by from 1 to 3 alkyl, halogenoalkyl, alkoxy, dialkylamino each having up to 4 carbon atoms in the alkyl moiety, halogen, phenyl, carboxyl, cyano, nitro and/or hydroxyl groups, or (b) a 5- or 6-membered heteroaromatic ring wherein the heteroatom is selected from nitrogen, oxygen and sulfur atoms and the ring is optionally anellated to a benzene nucleus; $R^2$ represents a hydrogen atom, or an alkyl group having up to 3 carbon atoms, a phenyl group or a cycloalkyl group having up to 6 carbon atoms in the ring and optionally bearing a hydrocarbon bridging radical having up to 2 carbon atoms; $R^3$ represents a hydrogen atom, or a hydroxy or acyloxy group; $R^4$ and $R^5$, which may be the same or different, each represents a hydrogen or halogen atom, or an alkyl or halogenoalkyl group each having up to 3 carbon atoms, or a nitro group; and X represents a nitrogen atom or a methine group) and physiologically acceptable acid addition salts thereof.

When $R^3$ in the compounds of formula I represents an acyloxy group, the aryl moiety is preferably derived from a straight-chained or branched alkane carboxylic acid having up to 6 carbon atoms and most preferably from nicotinic acid.

Preferred compounds of general formula I are those in which $R^1$ represents a phenyl group optionally substituted by one or more halogen atoms;

$R^2$ represents a hydrogen atom or an alkyl group having up to 3 carbon atoms;

$R^3$ represents a hydrogen atom or a hydroxy or nicotinoyloxy group;

$R^4$ and $R^5$, which may be the same or different, each represents a hydrogen or halogen atom or a methyl group; and X represents a nitrogen atom.

The novel compounds of formula I and their acid addition salts exhibit interesting pharmacological properties, in particular compounds which we have tested have exhibited hypolipaemic properties, together with a uric acid and blood sugar decreasing activity. These compounds also show good compatibility, and are therefore particularly suitable for treating hyperlipaemia.

Particularly preferred compounds of general formula I by virtue of their favourable pharmacological properties are:

O-{3-[4-(2-chlorophenyl)-piperazino]-2-hydroxypropyl}-4-chlorobenzaldoxime,

O-{3-[4-(2,6-dimethylphenyl)-piperazino]-2-hydroxypropyl}-4-chlorobenzaldoxime, and physiologically acceptable acid addition salts thereof.

Compounds of formula I according to the invention may be prepared by linking compounds having the structural element

(II)

with compounds having a group

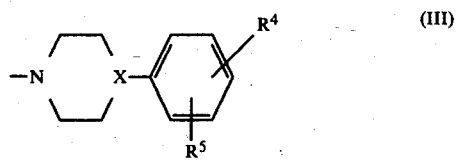
(III)

via the bridging group

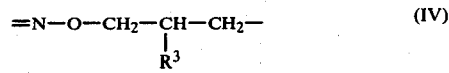
(IV)

(wherein $R^1$, $R^2$, $R^3$, $R^4$, $R^5$ and X are as hereinbefore defined).

Thus, according to further aspects of the present invention there are provided the following processes for the preparation of compounds of formula I, which processes comprise:

(A) reacting a carbonyl compound of formula

(V)

(in which $R^1$ and $R^2$ are as hereinbefore defined) or a reactive derivative thereof with a hydroxylamine derivative of formula

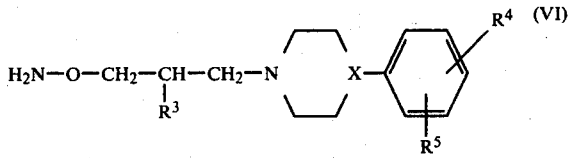
(VI)

(wherein $R^3$, $R^4$, $R^5$ and X are as hereinbefore defined) or an acid addition salt thereof;

(B) reacting an oxime of formula

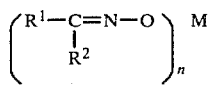

(in which $R^1$ and $R^2$ are as hereinbefore defined, M represents a hydrogen atom or an alkali metal or alkaline earth metal cation, and n represents the integer 1 when M is hydrogen or the valency of the cation when M represents an alkali metal or alkaline earth metal cation) with (B1) a substituted propyl compound of formula

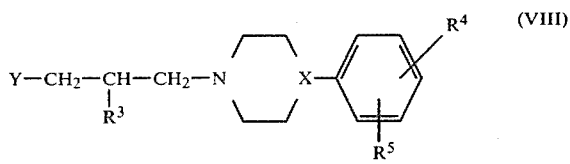

(in which $R^3$, $R^4$, $R^5$ and X are as hereinbefore defined and Y represents a halogen, preferably a chlorine or bromine, atom or a reactive sulphonic acid ester group, or Y together with $R^3$ and the two carbon atoms to which they are attached form an oxirane ring) or a salt thereof; or (B2) a propyl derivative of formula

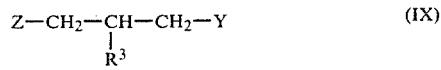

(in which $R^3$ and Y are as hereinbefore defined and Z represents a halogen, preferably a chlorine or bromine atom, or a reactive sulphonic acid ester group) to form an O-alkylated oxime of formula

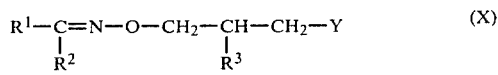

(in which $R^1$, $R^2$, $R^3$ and Y are as hereinbefore defined) which is subsequently reacted with an amine of formula

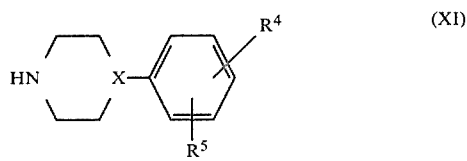

(in which $R^4$, $R^5$ and X are as hereinbefore defined); or (C) acylating a compound of formula I in which $R^3$ represents a hydroxy groups.

The reaction products of the above processes can be isolated as the free bases of the compounds of formula I or preferably converted with suitable acids to their physiologically acceptable acid addition salts.

Acylation of compounds of formula I according to the invention in which $R^3$ represents a hydroxy group according to process (C) can be effected with carboxylic acids, and can be carried out, for example, in the presence of condensation agents such as carbodiimides. Acylation is however especially preferred using carboxylic acids in the form of their reactive functional derivatives such as acid halides, anhydrides or reactive esters.

Examples of carbonyl compounds of formula V to be used in process (A) are, for example, aldehydes such as benzaldehyde and substituted derivatives thereof such as 4-methyl-, 4-phenyl-, 4-fluoro-, 2- or 4-chloro-, 3-trifluoromethyl-, 4-methoxy-, 4-dimethylamino-, 4-cyano-, 3-nitro-, 4-hydroxy-3-methoxy-, and 4-hydroxy-3-carboxybenzaldehyde; 1- and 2-naphthaldehyde; and heteroaromatic aldehydes, such as, 2-thienyl-, 2-, 3- or 4-pyridyl-, 3-chromon- and 3-indolyl aldehyde. Ketones, such as, for example, acetophenone, 4-chloroacetophenone, phenyl-1-norbornyl-ketone and the three different isomers of benzoyl pyridine.

These carbonyl compounds can also be used in the form of their reactive derivatives such as hemi- or full acetals, mercaptals, aminals or acylals. Also aldimines oximes (such as of formula VII), hydrazones, semicarbazones, thiosemicarbazones, cyanohydrins or bisulfite addition compounds may be used as starting substances.

Convenient compounds of formula VI for use in process (A), are appropriately substituted O-propyl hydroxylamines known from the literature or easily prepared by processes known in the literature, and the O-(2-hydroxypropyl)-hydroxylamines described in our co-pending U.S. Patent Application Ser. No. 850,057, filed Nov. 7, 1977, now abandoned, which are substituted in the 3-position of the propyl group by, for example, a 4-phenyl-, 4-(2,6-dimethylphenyl)-, 4-(2-chlorophenyl)- or 4-(3-trifluoromethylphenyl)-1-piperazino or -1-piperidyl group.

Oximes of formula VII for use in process (B) are known or can easily be prepared by methods known in the literature, for example, by reacting aldehydes or ketones of formula V with hydroxylamine and optionally with subsequent salt formation.

Starting substances of formula VIII for use in process (B1) are, for example, 1-(3-halogenopropyl)-, 1-(3-halogeno-2-hydroxypropyl)- and 1-(2,3-epoxypropyl)-piperazines and piperidines arylated in the 4-position analogously to compounds of formula VI.

Suitable starting materials of formula IX for the conversion of oximes of formula VII into intermediates of formula X in which $R^3$ and Y together with the two carbon atoms to which they are attached form an oxirane ring are, for example, epoxides such as epibromohydrin, 2,3-epoxypropyl-benzene sulphonate, -p-toluene sulphonate, -methane sulphonate and preferably epichlorohydrin; as well as 1,3-dihalogeno-2-propanols such as 1,3-dichloro-, 1,3-dibromo- and 1-bromo-3-chloro-2-propanol.

Intermediates of formula X in which $R^3$ represents a hydrogen atom may be preferably prepared using 3-halogenopropyl sulphonates or 1,3-dihalogeno-propanes of formula IX, especially 1-bromo-3-chloropropane.

Convenient amines of formula XI for use in process (B) are, for example, 4-phenyl-, 4-(2- or 3-methylphenyl)-, 4-(2,6- or 3,4-dimethylphenyl)-, 4-(2-,3- or 4-chlorophenyl)-, 4-(3-trifluoromethylphenyl)- and 4-(2-nitrophenyl)-piperazines or -piperidines.

The processes according to the invention are conveniently carried out in a solvent or dispersion agent.

Process (A) is preferably effected using equimolar quantities of the reaction materials in an aqueous-alcoholic solution. However, it is also possible to use other solvents which are inert under the reaction conditions, such as, for example, pyridine, dimethylformamide and alcohols such as methanol, ethanol, the various propanols or butanols and mixtures of these solvents. The hydroxylamine derivatives of formula VI are advantageously used in the form of their acid addition salts such as hydrochlorides, hydrobromides or sulphates. In the latter case, it is preferred to use at least a stoichiometric quantity of an acid binding agent in the reaction mixture, suitable acid binding agents being, for example, alkali metal or alkaline earth metal hydroxides or carbonates or organic bases such as triethylamine. The condensation reaction is advantageously carried out at a temperature of from 0° C. to the boiling point of the reaction mixture, preferably from 50° to 100° C. and most preferably from 50° to 80° C. The reaction time ranges from a few minutes to a few hours.

Alkylation of the oximes of formula VII with compounds of formula VIII or IX according to process B may be carried out, for example, in anhydrous alcohols, hydrocarbons, or aprotic solvents and also in an excess of the alkylating agent used. The alkylation of the oximes is preferably effected in the presence of a base such as an alkali metal or alkaline-earth metal hydroxide, carbonate, hydride or alcoholate or an organic base, for example, triethylamine, pyridine, picoline or quinoline. Alternatively alkali metal or alkaline-earth metal oximates prepared separately may if desired be used. Alcohols which may be used for the solvent include, among others, methanol, ethanol, propanol, isopropanol and the various butanols (e.g., isobutanol). Hydrocarbon solvents include, for example, hexane, cyclohexane, benzene, toluene and xylene. Suitable aprotic solvents are, for example, dimethylformamide, dimethylacetamide, N-methyl-pyrrolidone, tetramethylurea, hexamethyl phosphoric acid trisamide and dimethylsulphoxide. Depending on the particular process, the reaction temperature is generally from 0° C. to the boiling point of the reaction mixture; however, it is preferably above 20° C. When effected in an alcoholic solvent the temperature used is preferably from 50° to 100° C. and in an aprotic solvent from 80° to 120° C., e.g. about 100° C. The reaction times are generally between 1 and 10 hours.

Reaction of intermediates of formula X in which Y represents halogen or a reactive sulphonic acid ester group with amines of formula XI is advantageously effected under similar conditions to the first stage of process B2. Aminolysis of O-(2,3-epoxypropyl)-oximes of formula X (in which $R^3$ and Y together represent an oxygen atom) with amines of formula XI preferably takes place, however, by heating for 1 to 5 hours in higher-boiling point alcohols such as n-propanol, isopropanol, n-butanol or isobutanol in the absence of other bases. The starting materials are preferably used in equimolar quantities.

Suitable acids for the formation of physiologically acceptable acid addition salts of compounds of general formula I according to the invention are, for example, halogen hydracids (especially hydrochloric acid), sulphuric acid, phosphoric acid and organic acids such as, for example, acetic acid, lactic acid, maleic acid, fumaric acid, oxalic acid, tartaric acid, citric acid, gluconic acid, p-toluenesulphonic acid, methanesulphonic acid and cyclohexylamidosulphonic acid.

It will be appreciated that compounds of formula I according to the invention may occur in stereoisomeric E and/or Z forms on the basis of known oxime isomerism. Also, when $R^3$ represents a hydroxy or acyloxy group, the compounds possess a chiral carbon atom and can thus exist in optically active D and/or L forms as well as racemic mixtures thereof. All such forms are intended to be within the scope of the invention.

The pure antipodes may be prepared either by effecting the reactions according to processes (A) and (B) using enantiomeric starting compounds of formula VI or VIII and IX or by resolving racemates of the products into the enantiomers by known processes, e.g. by fractional crystallisation of the diastereomeric acid addition salts formed with an optically active acid.

As indicated above the novel compounds of formula I and their physiologically compatible salts possess interesting pharmacological properties and may therefore be useful in human and/or veterinary medicine, in particular for the treatment of hyperlipoproteinaemias and/or arteriosclerosis. The compounds according to the invention may be administered either alone or mixed with suitable pharmaceutical carriers or excipients.

Thus, according to a further aspect of the invention there is provided a pharmaceutical composition comprising as active ingredients at least one compound of formula I or a physiologically acceptable acid addition salts thereof in association with a pharmaceutical carrier or excipient.

The compositions according to the invention are preferably administered in a form suitable for oral, rectal or parenteral administration. Such forms may be, for example, tablets, capsules, solutions, powders, granulates, emulsions, syrups, coated tablets, suppositories, injectable solutions and forms adapted to provide a sustained release of active ingredient. These forms of administration may be formulated with carriers and excipients conventional to the pharmaceutical art. It is possible however to administer the compounds according to the invention without the addition of carriers or excipients such as in the form of microcapsules.

Carriers which may be used in the compositions are for example, magnesium carbonate, various sugars, starch, cellulose derivatives, gelatin, animal and vegetable oils, polyethylene glycols and solvents.

The compositions according to the invention are preferably in the form of dosage units. Suitable dosages for human administration being 1 to 1000, preferably 1 to 200 and desirably 2 to 80 mg per day, and for animals (e.g. rats) 0.03 to 100 and preferably 0.1 to 10 mg/kg/day.

If desired, the compositions according to the invention may additionally comprise one or more further pharmacologically active ingredients such as, for example, blood-circulatory agents, anti-diabetic agents and anti-uricopathic agents.

Pharmacological Tests and Results

It is at present generally believed that in addition to hyperuricaemia and diabetes, increased serum lipid values may be important factors in the incidence of arteriosclerotic ailments, not only in the coronary blood vessels. There is thus, a growing interest in compounds having multifunctional involvement in disturbed lipid, blood sugar and uric acid metabolism.

We have found that the O-alkyloximes of formula I and the physiologically acceptable acid addition salts thereof can reduce lipid levels in serum and have very low acute toxicities. In this respect, our tests show that their activity in simultaneously decreasing blood sugar and uric acid levels is particularly favourable.

Hypolipaemic activity has been tested in a standard test on male rats having a normal serum-lipid content, using Clofibrat [ethyl 2-(p-chlorophenoxy)isobutyrate] as comparative substance. The test period extended over 8 days. Administration of the compounds was effected orally once a day using a pharyngeal probe in doses of 10,3,1 and 0.3 mg/kg. Blood samples were generally taken before and after treatment. The cholesterol concentration in the serum was determined by the method of K. Lauber and R. Richterich (Klin. Wochenschrift 40 (1962) 1252) and the triglyceride concentration by the method of M. Eggstein and F. H. Kreutz (loc. cit. 44 (1966) 262,267). The results calculated from this measured data for a reduction in the serum-lipid content are set out in table 1.

Analysis: Calculated: C 67.28%; H 7.26%; Cl 9.46%; N 7.47%. Found: C 67.21%; H 7.34%; Cl 9.41%; N 7.19%.

EXAMPLE 2

O-[3-(4-Phenylpiperazino)-2-nicotinoyloxy-propyl]-benzaldoxime hydrochloride (According to process C)

A solution of 16.5 g (0.04 mol) of O-[3-(4-phenylpiperazino)-2-hydroxypropyl]-benzaldoxime dihydrochloride and 6.6 g (0.04 mol) of nicotinoyl chloride hydrochloride in 200 ml of anhydrous pyridine are

| Compound of Example | % change in standard test after 8 oral applications of mg/kg/day ||||||
| | 10 || 3 || 0.3 ||
| | Serum-Cholesterol | Serum-triglyceride | Serum-Cholesterol | Serum-triglyceride | Serum-Cholesterol | Serum-triglyceride |
| --- | --- | --- | --- | --- | --- | --- |
| 2  | −43/−43 | −35/−35 | −35/−32 |         | −19/−16 |         |
| 4  | −69/−73 | −27/−15 |         |         |         |         |
| 5  | −58/−50 | −48/−43 |         |         | −34/−28 | −24/−16 |
| 6  | −47/−36 | −24/−18 | −37/−24 | −35/−22 |         |         |
| 12 | −35/−23 | −38/−37 | −42/−23 | −39/−31 |         |         |
| 25 | −62/−73 | −27/−16 |         |         |         |         |
| 27 | −62/−51 | −39/−38 |         |         | −20/−12 | −30/−22* |
| 30 |         |         | −64/−67 | −24/−29 |         |         |
| 40 | −67/−66 | −55/−39 |         |         |         |         |
| Clofibrat | inactive | inactive |     |         |         |         |

*1 mg/kg/day

The values in front of the inclined stroke in the top columns represent the percentage variation in the post-treatment value in relation to the initial pre-treatment value of the preparation group, the pre-treatment value equalling 100%; the values after the stroke give the percentage change in the post-treatment value of the treated group in relation to the post-treatment value (= 100%) of a running placebo group.

The following Examples illustrate the preparation of compounds according to the invention. The structure of the compounds described has been proved by elemental analysis and by i.r. and $^1$H-n.m.r spectra.

EXAMPLE 1

O-[3-(4-Phenylpiperidino)-2-hydroxypropyl]-benzaldoxime hydrochloride (According to process B2)

To a solution of 5.75 g (0.25 gram atom) of sodium in 250 ml of anhydrous ethanol was added 30.3 g (0.25 mol) of benzaldoxime. The reaction mixture was stirred for 30 minutes at room temperature and the alcohol evaporated off under reduced pressure. The dried sodium oximate obtained is added, in portions with stirring at 80° C., to 156 ml (2 mol) of epichlorohydrin over 30 minutes and kept at this temperature for a further 5 hours. After cooling, the solution is filtered from the precipitated sodium chloride and excess epichlorohydrin is distilled off under reduced pressure. Fractional distillation of the oily residue under reduced pressure yields 29.2 g (65.9% of theory) of O-(2,3-epoxypropyl)-benzaldoxime of boiling point (0.3 mm/Hg) 121°-124° C.

17.7 g (0.1 mol) of this oxime and 16.1 g (0.1 mol) of 4-phenylpiperidine are refluxed for 6 hours in 100 ml of isopropanol. After the addition of an equivalent quantity of ethanolic hydrochloric acid the crude hydrochloride is precipitated and is recrystallised from ethanol with the addition of diethyl ether at boiling heat until turbidity.

Yield: 30.4 g (81% of theory); melting point: 161°-163° C. $C_{21}H_{27}ClN_2O_2$ (M.W.=374.9).

heated for 8 hours with stirring to 60° C. The reaction mixture is then evaporated under reduced pressure and the oily residue is dissolved in ethyl acetate and acidified with 0.04 mol of ethanolic hydrochloric acid, the monohydrochloride thereupon being precipitated as a crystalline deposit. The product is recrystallised from ethanol with the addition of diethyl ether at boiling heat until turbidity.

Yield: 14.2 g (74.0% of theory); melting point: 179°-181° C. $C_{26}H_{29}ClN_4O_3$ (M.W.=481.0).

Analysis: Calculated: C 64.93%; H 6.08%; Cl 7.37%; N 11.65%. Found: C 64.79%; H 6.15%; Cl 7.41%; N 11.61%.

EXAMPLE 3

O-[3-(4-Phenylpiperazino)-2-hydroxypropyl]-4-tolylaldoxime dihydrochloride (According to process B1)

To a solution of 2.3 g (0.1 gram atom) of metallic sodium in 250 ml of anhydrous ethanol is added, at room temperature, 13.5 g (0.1 mol) of 4-tolylaldoxime, the mixture is then stirred for 30 minutes and subsequently 25.5 g (0.1 mol) of 1-(4-phenylpiperazino)-2-hydroxy-3-chloropropane are added. After refluxing for 5 hours, the reaction mixture is evaporated under reduced pressure, and the residue is dissolved in 250 ml of chloroform and extracted several times with water. From the organic phase, after drying over sodium sulphate and evaporation under reduced pressure, there is obtained an oily crude base which is dissolved in ethyl acetate to convert it into the dihydrochloride by addition of 0.2 mol of ethanolic hydrochloric acid. Repeated recrystallisation from ethanol yields 25.8 g (60.6% of theory) of the title compound of melting point 194°–195° C. (decomposition). $C_{21}H_{29}Cl_2N_3O_2$ (M.W.=426.4).

Analysis: Calculated: C 59.15%; H 6.85%; Cl 16.62%; N 9.85%. Found: C 59.20%; H 7.02%; Cl 16.65%; N 9.55%.

EXAMPLE 4

O-[3-(4-(2-Chlorophenyl)-piperazino)-propyl]-4-chlorobenzaldoxime hydrochloride (According to process B1)

To a solution of 1.4 g (0.06 gram atom) of metallic sodium in 150 ml of anhydrous ethanol is added, at room temperature, 8.6 g (0.06 mol) of 4-chlorobenzaldoxime, the mixture is stirred for 30 minutes and 16.4 g (0.06 mol) of 1-[4-(2-chlorophenyl)-piperazino]-3-chloropropane are then added. After heating for 8 hours under reflux, the reaction mixture is evaporated under reduced pressure, the residue dissolved in water and extracted several times with chloroform. The combined organic extracts are dried over sodium sulphate and again concentrated to dryness. The oily residue obtained is dissolved in ethyl acetate and converted with ethanolic hydrochloric acid into the hydrochloride which is repeatedly recrystallised from ethanol with the addition of diethyl ether.

Yield: 16.4 g (63.8% of theory), melting point 212°–213° C. $C_{20}H_{24}Cl_3N_3O$ (M.W.=428.8)

Analysis: Calculated: C 56.02%; H 5.64%; Cl 24.80%; N 9.79%. Found: C 56.16%; H 5.87%; Cl 24.89%; N 9.82%.

EXAMPLE 5

O-[3-(4-(2-Chlorophenyl)-piperazino)-2-hydroxypropyl]-4-chlorobenzaldoxime hydrochloride (According to process A)

14.1 g (0.1 mol) of 4-chlorobenzaldehyde are dissolved in 300 ml of ethanol. After addition of 35.9 g (0.1 mol) of O-[3-(4-(2-chlorophenyl)-piperazino)-2-hydroxypropyl]hydroxylamine dihydrochloride in 90 ml of water, a solution of 10.6 g (0.1 mol) of sodium carbonate in 60 ml of water is added dropwise with stirring. The mixture is then stirred for 30 minutes at room temperature and then for 1 hour at 60°–70° C. The alcohol is distilled off under reduced pressure, the residue mixed with ethyl acetate and the sodium chloride is removed by repeated washing with with water. The organic phase yields after drying over sodium sulphate and evaporation under reduced pressure, the crude base (0.100%). This is then dissolved in ethyl acetate and mixed with 0.1 mol of ethanolic hydrochloric acid to convert it into the hydrochloride. The product precipitated is filtered off, washed with ether and optionally recrystallised from ethanol with the addition of ether at boiling heat until turbidity.

Yield: 35.7 g (80.3% of theory); melting point: 167°–168° C. $C_{20}H_{24}Cl_3N_3O_2$ (M.W.=444.8)

Analysis: Calculated: C 54.01%; H 45.44%; Cl 23.91%; N 9.45%. Found: C 54.07%; H 45.56%; Cl 23.71%; N 9.37%.

According to process B2, the title compound can be produced as follows via O-(2,3-epoxypropyl)-4-chlorobenzaldoxime as an intermediate stage: 17.9 g (0.1 mol) of 4-chlorobenzaldoxime are added to a solution of 2.3 g (0.1 gram atom) of metallic sodium in 200 ml of anhydrous ethanol, stirred for 30 minutes at room temperature and the alcohol removed under reduced pressure. The dried sodium salt is added, in portions at 80° C., with stirring to 78 ml (1 mol) of epichlorohydrin over 15 minutes and kept at this temperature for a further 5 hours. After filtering from precipitated sodium chloride and removing the excess epichlorohydrin under reduced pressure the oily residue is dissolved in methylene chloride. Extracting several times with water, drying the organic phase over sodium sulphate, concentrating under reduced pressure and re-crystallising the remaining oil from ethanol yields 12.5 g (59% of theory) of O-(2,3-epoxypropyl)-4-chlorobenzaldoxime of melting point 69°–70° C.

$C_{10}H_{10}ClNO_2$ (M.W.=211.7).

Analysis: Calculated: C 56.75%; H 4.76%; Cl 16.75%; N 6.62%. Found: C 56.51%; H 4.58%; Cl 16.26%; N 6.70%.

10.6 g (0.05 mol) of the epoxide are refluxed with 9.8 g (0.05 mol) of 1-(2-chlorophenyl)-piperazine in 50 ml of isopropanol for 4 hours. After cooling and addition of an equivalent quantity of ethanolic hydrochloric acid O-[3-(4-(2-chlorophenyl)-piperazino)-2-hydroxypropyl]-4-chlorobenzaldoxime hydrochloride is crystallised out slowly.

Yield: 20 g (90% of theory); melting point: 168°–169° C. The formulae of the compounds obtained by Examples 1 to 5 is shown in the following Table 2. The compounds listed therein have been prepared analogously by processes A, B or C.

TABLE 2

Examples of formula

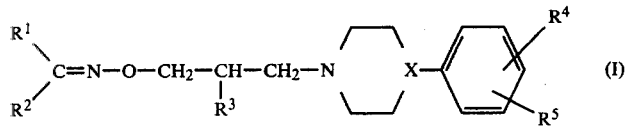

(I)

| Example | $R^1$ | $R^2$ | $R^3$ | X | $R^4$ | $R^5$ | Process | Isolated as | Melting point °C. |
|---------|-------|-------|-------|---|-------|-------|---------|-------------|-------------------|
| 1 | 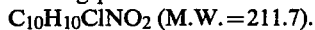 | H | HO— | CH | H | H | B | HCl | 161–163 |
| 2 | 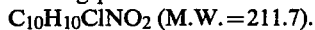 | H | (pyridine-C(=O)-O—) | N | H | H | C | HCl | 179–181 |

TABLE 2-continued

Examples of formula $$R^1R^2C=N-O-CH_2-CH(R^3)-CH_2-N\underset{}{\overset{}{\bigcirc}}X-\text{Ar}(R^4)(R^5) \quad (I)$$

| Example | $R^1$ | $R^2$ | $R^3$ | X | $R^4$ | $R^5$ | Process | Isolated as | Melting point °C. |
|---|---|---|---|---|---|---|---|---|---|
| 3 | 4-CH$_3$-C$_6$H$_4$- | H | HO— | N | H | H | B | 2 HCl | 194–195 (decomp.) |
| 4 | 4-Cl-C$_6$H$_4$- | H | H— | N | 2-Cl— | H | B | HCl | 212–213 |
| 5 | 4-Cl-C$_6$H$_4$- | H | HO— | N | 2-Cl— | H | A and B | HCl | 165–167 |
| 6 | C$_6$H$_5$- | H | HO— | N | H | H | B | 2 HCl | 183–184 |
| 7 | C$_6$H$_5$- | H | HO— | N | 2-CH$_3$— | H | B | HCl | 180–181 |
| 8 | C$_6$H$_5$- | H | HO— | N | 3-CH$_3$— | H | B | 2 HCl | 173–174 |
| 9 | C$_6$H$_5$- | H | HO— | N | 3-CH$_3$— | 4-CH$_3$— | B | HCl | 157–159 |
| 10 | C$_6$H$_5$- | H | HO— | N | 2-CH$_3$— | 6-CH$_3$— | B | HCl | 168–169 |
| 11 | C$_6$H$_5$- | H | HO— | N | 3-CF$_3$— | H | B | HCl | 196–197 |
| 12 | C$_6$H$_5$- | H | HO— | N | 2-Cl— | H | B | HCl | 130–131 |
| 13 | C$_6$H$_5$- | H | HO— | N | 3-Cl— | H | B | HCl | 180–183 |
| 14 | C$_6$H$_5$- | H | HO— | N | 4-Cl— | H | B | HCl | 144–145 |
| 15 | C$_6$H$_5$- | H | HO— | N | 2-NO$_2$— | H | B | HCl | 140–142 |
| 16 | 1-naphthyl- | H | HO— | N | 2-CH$_3$— | 6-CH$_3$— | A | HCl | 165–167 |
| 17 | 2-naphthyl- | H | HO— | N | 2-Cl— | H | A | HCl | 160–162 |
| 18 | 3-CF$_3$-C$_6$H$_4$- | H | HO— | N | H | H | A | 2 HCl | 190–191 (decomp.) |
| 19 | 4-CH$_3$O-C$_6$H$_4$- | H | HO— | N | 2-CH$_3$— | 6-CH$_3$— | A | HCl | 204–206 |

TABLE 2-continued

Examples of formula $$R^1R^2C=N-O-CH_2-CH(R^3)-CH_2-N\underset{}{\overset{}{\diagdown}}\text{piperazine}\diagup X-\text{phenyl}(R^4)(R^5) \quad (I)$$

| Example | $R^1$ | $R^2$ | $R^3$ | X | $R^4$ | $R^5$ | Process | Isolated as | Melting point °C. |
|---|---|---|---|---|---|---|---|---|---|
| 20 | 4-CH₃O-phenyl | H | HO— | N | 2-Cl— | H | A | HCl | 157–159 |
| 21 | 4-(CH₃)₂N-phenyl | H | HO— | N | H | H | A | 3 HCl | 135–137 |
| 22 | 2-Cl-phenyl | H | HO— | CH | H | H | B | HCl | 195–196 |
| 23 | 4-F-phenyl | H | HO— | N | H | H | A | 2 HCl | 187–188 |
| 24 | 2-Cl-phenyl | H | HO— | N | H | H | B | 2 HCl | 176–177 |
| 25 | 4-Cl-phenyl | H | HO— | N | H | H | B | HCl | 149–150 |
| 26 | 2-Cl-phenyl | H | H | N | 2-Cl— | H | B | HCl | 142–143 |
| 27 | 4-Cl-phenyl | H | HO— | N | 2-CH₃— | 6-CH₃— | A | HCl | 197–199 |
| 28 | 2-Cl-phenyl | H | HO— | N | 2-Cl— | H | B | HCl | 149–150 |
| 29 | 2-Cl-phenyl | H | HO— | N | 4-Cl— | H | B | HCl | 174–175 |
| 30 | 4-Cl-phenyl | H | HO— | N | 4-Cl— | H | B | HCl | 173–175 |
| 31 | biphenyl-4-yl | H | HO— | N | 2-CH₃— | 6-CH₃— | A | HCl | 210–212 |
| 32 | 2-HO-3-COOH-phenyl | H | HO— | N | H | H | A | 2 HCl | 205–206 (decomp.) |
| 33 | 4-NC-phenyl | H | HO— | N | H | H | A | 2 HCl | 216–218 |
| 34 | 3-NO₂-phenyl | H | HO— | N | 3-CF₃— | H | B | HCl | 201–203 |

TABLE 2-continued

Examples of formula

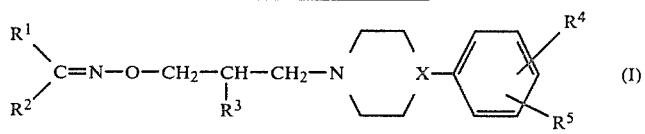

(I)

| Example | $R^1$ | $R^2$ | $R^3$ | X | $R^4$ | $R^5$ | Process | Isolated as | Melting point °C. |
|---|---|---|---|---|---|---|---|---|---|
| 35 | CH₃O, HO-phenyl | H | HO— | N | H | H | A | 2 HCl | 199–200 |
| 36 | thienyl | H | HO— | N | H | H | A | 2 HCl | 193 (decomp.) |
| 37 | pyridyl | H | HO— | N | H | H | A | 3 HCl | 216–217 |
| 38 | indolyl | H | HO— | N | H | H | A | 2 HCl | 140–143 |
| 39 | phenyl | CH₃— | HO— | N | 2-Cl— | H | B | HCl | 160–162 |
| 40 | Cl-phenyl | CH₃— | HO— | N | 2-Cl— | H | B | HCl | 197–198 |
| 41 | phenyl | cyclopentyl | H | N | H | H | B | 2 HCl | 98–101 |
| 42 | phenyl | cyclopentyl | H | N | 2-CH₃— | H | B | 2 HCl | 108–111 |
| 43 | pyridyl | phenyl | H | N | H | H | B | 2 HCl | 190–193 |
| 44 | pyridyl | phenyl | H | N | 2-CH₃— | H | B | 3 HCl | 151–153 |
| 45 | pyridyl | phenyl | H | N | 2-CH₃— | H | B | 3 HCl | 117–119 |
| 46 | pyridyl | phenyl | H | N | 2-CH₃— | H | B | 3 HCl | 149–152 |

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. Compounds of general formula

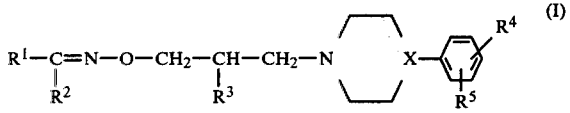

wherein R¹ is a member selected from the group consisting of (a1) an unsubstituted at most binuclear aryl group having 6 to 10 carbon atoms, and (a2) a group as in (a1) but substituted by from 1 to 3 equal or different radicals selected from the group consisting of alkyl, halogenoalkyl, alkoxy, dialkylamino each having up to 4 carbon atoms in the alkyl moiety, halogen, phenyl, carboxyl, cyano, nitro and hydroxy groups, (b) a 5- to 6-membered heteroaromatic ring containing one heteroatom which is selected from the group consisting of nitrogen, oxygen and sulfur atoms and such rings anellated to a benzene nucleus and the non-heteroatoms of the ring are carbon atoms; and R² is a member selected from the group consisting of hydrogen, alkyl having up to 3 carbon atoms, phenyl, cycloalkyl having up to 6 carbon atoms in the ring and cycloalkyl bearing a hydrocarbon bridging radical having up to 2 carbon atoms;

R³ is hydrogen, hydroxy, alkanoyloxy or nicotinoyloxy; and

R⁴ and R⁵ are the same or different and each is a member selected from the group consisting of hydrogen, halogen, alkyl, and halogenoalkyl each having up to 3 carbon atoms, and nitro; and X is nitrogen or methine; and
physiologically acceptable acid addition salts thereof.

2. Compounds of general formula

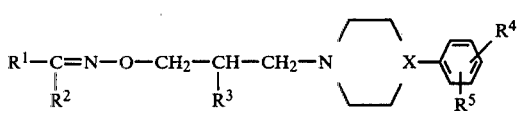

wherein
R¹ is a member selected from the group consisting of unsubstituted phenyl or phenyl substituted by at least one halogen atom;
R² is a member selected from the group consisting of hydrogen or alkyl having up to 3 carbon atoms;
R³ is a member selected from the group consisting of hydrogen or hydroxy or nicotinoyloxy;
R⁴ and R⁵ are members independently selected from the group consisting of hydrogen, halogen and methyl; and
X is nitrogen;
and physiologically acceptable acid addition salts thereof.

3. Compounds of general formula

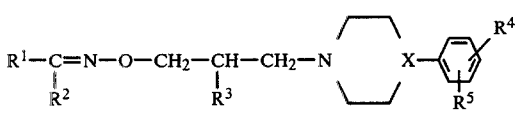

wherein
R¹ is a member selected from the group consisting of
(a1) an unsubstituted at most binuclear aryl group having from 6 to 10 carbon atoms; and
(a2) a group as in (a1) but substituted by from 1 to 3 equal or different radicals selected from the group consisting of alkyl, halogenoalkyl, alkoxy, dialkylamino each having up to 4 carbon atoms in the alkyl moiety, halogen, phenyl, carboxyl, cyano, nitro and hydroxy groups, (b) a 5- to 6-membered heteroaromatic ring containing one heteroatom which is selected from nitrogen, oxygen and sulfur atoms and such rings anellated to a benzene nucleus and the nonheteroatoms of the ring are carbon atoms;

R² is a member selected from the group consisting of hydrogen, alkyl having up to 3 carbon atoms, phenyl, cycloalkyl having up to 6 carbon atoms in the ring and cycloalkyl bearing a hydrocarbon bridging radical having up to 2 carbon atoms;

R³ is a member selected from the group consisting of alkanoyloxy of one to six carbon atoms and nicotinoyloxy; and R⁴ and R⁵ are the same or different and each is a member selected from the group consisting of hydrogen, halogen, alkyl, and halogenoalkyl each having up to 3 carbon atoms, and nitro; and X is nitrogen or methine; and physiologically acceptable acid addition salts thereof.

4. O-{3-[4-(2-Chlorophenyl)-piperazino]-2-hydroxypropyl}-4-chlorobenzaldoxime and physiologically acceptable acid addition salts thereof.

5. O-{3-[4-(2,6-Dimethylphenyl)-piperazino]-2-hydroxypropyl}-4-chlorobenzaldoxime and physiologically acceptable acid addition salts thereof.

6. Compounds of general formula:

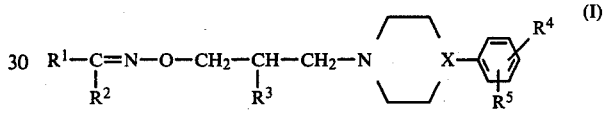

wherein R¹ is a member selected from the group consisting of:
(a1) an unsubstituted at most binuclear aryl group having 6 to 10 carbon atoms,
(a2) a group as in (a1) but substituted by from 1 to 3 equal or different radicals selected from the group consisting of alkyl, halogenoalkyl, alkoxy, dialkylamino each having up to 4 carbon atoms in the alkyl moiety, halogen, phenyl, carboxyl, cyano, nitro and hydroxy groups, R² is a member selected from the group consisting of hydrogen, alkyl having up to 3 carbon atoms, phenyl, cycloalkyl having up to 6 carbon atoms in the ring and cycloalkyl bearing a hydrocarbon bridging radical having up to 2 carbon atoms; and R³ is hydrogen, hydroxy, alkanoyloxy or nicotinoyloxy; and R⁴ and R⁵ are the same or different and each is a member selected from the group consisting of hydrogen, halogen, alkyl, and halogenoalkyl each having up to 3 carbon atoms, and nitro; and X is nitrogen or methine; and
physiologically acceptable acid addition salts thereof.

7. A pharmaceutical composition for decrease of blood cholesterol comprising an effective amount of a compound of claim 1 and a pharmaceutically acceptable carrier or excipient.

8. The composition of claim 7 wherein the composition contains between 1 and 1,000 milligrams of compound of claim 1 per dosage unit.

9. A pharmaceutical composition for decrease of blood triglyceride level comprising an effective amount of a compound of claim 1 and a pharmaceutically acceptable carrier or excipient.

10. The composition of claim 9 wherein the composition contains between 1 and 1,000 milligrams of compound of claim 1 per dosage unit.

* * * * *